US012779192B2

(12) United States Patent
Guo

(10) Patent No.: US 12,779,192 B2
(45) Date of Patent: Nov. 3, 2026

(54) VALVE GASKET AND HEMOSTASIS VALVES AND CANNULA UNITS INCORPORATING THE SAME

(71) Applicant: St. Jude Medical, Cardiology Division, Inc., St. Paul, MN (US)

(72) Inventor: Xiaoping Guo, Eden Prairie, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 426 days.

(21) Appl. No.: 18/560,978

(22) PCT Filed: May 10, 2022

(86) PCT No.: PCT/US2022/028566
§ 371 (c)(1),
(2) Date: Nov. 15, 2023

(87) PCT Pub. No.: WO2022/245598
PCT Pub. Date: Nov. 24, 2022

(65) Prior Publication Data

US 2024/0252802 A1 Aug. 1, 2024

Related U.S. Application Data

(60) Provisional application No. 63/191,703, filed on May 21, 2021.

(51) Int. Cl.
*A61M 39/06* (2006.01)
*A61M 39/02* (2006.01)

(52) U.S. Cl.
CPC ... *A61M 39/0606* (2013.01); *A61M 2039/027* (2013.01); *A61M 2039/0626* (2013.01);
(Continued)

(58) Field of Classification Search
CPC .......... A61M 39/0606; A61M 39/0693; A61M 2039/0633; A61M 2039/064;
(Continued)

(56) References Cited

U.S. PATENT DOCUMENTS 5,269,763 A * 12/1993 Boehmer .......... A61M 39/0606 604/167.04
5,456,284 A * 10/1995 Ryan ...................... A61B 1/018 604/167.04

(Continued)

FOREIGN PATENT DOCUMENTS

CA 2327657 A1 9/1999
CN 112717269 A * 4/2021 ............ A61M 39/06

OTHER PUBLICATIONS

International Search Report and Written Opinion for International Application No. PCT/US2022/028566 mailed Aug. 22, 2022.

*Primary Examiner* — Andrew M Gilbert
(74) *Attorney, Agent, or Firm* — Wiley Rein LLP

(57) ABSTRACT

A gasket for a hemostasis valve includes an annular wall, a membrane, a central protrusion on the membrane, and a plurality of ligaments attached to the central protrusion extending radially to the annular wall. The membrane, central protrusion, and ligaments are divided by slits into a plurality of flaps, with each flap bounded along an outer circumferential edge by the annular wall, along an inner circumferential edge by the central protrusion, and along its radial edges by segments of the ligaments. Two such gaskets can be arranged, back-toback, in a hemostasis valve. To facilitate such assembly, each gasket can include a plurality of positioning protrusions extending axially and a plurality of positioning recesses set into a circumferential surface, with the protrusions and recesses having complementary shapes for proper interconnection and fit between gaskets.

21 Claims, 11 Drawing Sheets

(52) U.S. Cl.
CPC ................. *A61M 2039/064* (2013.01); *A61M 2039/0666* (2013.01); *A61M 2039/0673* (2013.01); *A61M 2039/0686* (2013.01)

(58) Field of Classification Search
CPC .... A61M 2039/0646; A61M 2039/066; A61M 2039/0666; A61M 2039/0673; A61M 2039/0686
See application file for complete search history.

(56) References Cited

U.S. PATENT DOCUMENTS

| | | | | | |
|---|---|---|---|---|---|
| 5,968,068 | A * | 10/1999 | Dehdashtian | A61F 2/958 604/164.08 |
| 6,024,729 | A * | 2/2000 | Dehdashtian | A61M 39/0606 604/167.04 |
| 6,551,283 | B1 * | 4/2003 | Guo | A61M 39/06 251/149.1 |
| 9,545,632 | B2 * | 1/2017 | Lentz | B01L 3/56 |
| 2001/0053895 | A1 * | 12/2001 | Vaillancourt | A61M 39/045 604/243 |
| 2002/0010425 | A1 * | 1/2002 | Guo | A61M 39/06 604/167.04 |
| 2005/0010238 | A1 | 1/2005 | Potter et al. | |
| 2009/0012476 | A1 * | 1/2009 | Catlin | A61M 39/0606 604/167.04 |
| 2011/0282286 | A1 * | 11/2011 | Argentine | A61M 25/0097 604/167.03 |
| 2014/0074035 | A1 * | 3/2014 | De | A61M 39/20 604/167.04 |
| 2014/0276434 | A1 * | 9/2014 | Woehr | A61M 39/0606 604/167.03 |
| 2015/0190570 | A1 * | 7/2015 | Teoh | A61M 39/0613 29/428 |
| 2015/0306349 | A1 * | 10/2015 | Bonnal | A61M 25/0097 604/272 |
| 2017/0326341 | A1 | 11/2017 | Liska | |
| 2019/0351210 | A1 * | 11/2019 | Solomon | A61M 25/0075 |
| 2020/0188634 | A1 * | 6/2020 | Woehr | A61M 25/0097 |
| 2021/0113824 | A1 * | 4/2021 | Chng | A61B 5/15003 |

* cited by examiner

VALVE GASKET AND HEMOSTASIS VALVES AND CANNULA UNITS INCORPORATING THE SAME

CROSS-REFERENCE TO RELATED APPLICATIONS

This application claims the benefit of U.S. provisional application No. 63/191,703, filed 21 May 2021, which is hereby incorporated by reference as though fully set forth herein.

BACKGROUND

The present disclosure relates generally to medical devices and instruments. More particularly, the instant disclosure relates to valve gaskets, hemostasis valves and hemostasis cannula units containing such gaskets.

A variety of cardiovascular procedures, such as electrophysiology (EP) mapping and ablation, delivery and implantation of implantable cardioverter defibrillator (ICD) leads, percutaneous transluminal coronary angiography (PTCA), angioplasty, and the like, require vascular access for corresponding interventional medical devices (e.g., EP catheters, ICD leads, PTCA balloon catheters, etc.). Several techniques for introducing such devices into a patient's vasculature, such as the cut-down method and the Seldinger technique, are known.

The Seldinger technique involves surgically opening a vasculature of a patient with a relatively small incision and a needle, followed by inserting a guidewire into the vein or artery through the lumen of the needle. After removing the needle, a cylindrical dilator associated with a cylindrical introducer is inserted over the directing guidewire, followed by the advancement of the introducer along the directing dilator or guidewire into the vasculature until the distal end of the introducer sheath reaches the targeted location of the vasculature or anatomical structure (e.g., the heart) for an intended medical procedure. After removing the guidewire and dilator, the central lumen of the introducer sheath will establish a safe cardiovascular passageway of access to the blood vessel or anatomical structure, thus allowing for repetitive insertion and withdrawal of various interventional medical devices into and from the patient's vasculature, respectively.

To minimize blood loss or leakage from the distal opening of an introducer sheath, and to reduce the risk of air embolism during and after the Seldinger process, such an introducer sheath can be fit with a hemostasis valve system at the front of the proximal opening of the introducer sheath. The hemostasis valve system typically includes one or more valve gaskets contained within an introducer housing, also referred to as a cannula.

BRIEF SUMMARY

Disclosed herein is a valve gasket, including: an annular wall; a plurality of ligaments attached to and extending radially inward from the annular wall, wherein each ligament of the plurality of ligaments includes a ligament slit that divides the ligament into two ligament segments; and a membrane surrounded by the annular wall and attached to the plurality of ligaments and to the annular wall, wherein the membrane includes at least one membrane slit that divides the membrane into a plurality of flaps, wherein the plurality of ligaments are positioned with the plurality of ligament slits aligned with the at least one membrane slit, such that each flap is bounded along a circumferential edge by the annular wall, along a first radial edge by a first ligament segment, and along a second radial edge by a second ligament segment.

The valve gasket may also include a central protrusion positioned on the membrane, wherein the plurality of ligaments connect to the central protrusion. The central protrusion also includes a plurality of central protrusion slits that are aligned with the plurality of ligament slits, and thus the at least one membrane slit. In some embodiments of the disclosure, the central protrusion includes a guiding recess to facilitate insertion of an interventional medical device through the membrane.

According to aspects of the disclosure, the annular wall includes: a cylindrical portion; a beveled portion; a plurality of positioning protrusions extending axially from an exit surface of the cylindrical portion; and a plurality of positioning recesses extending radially into a circumferential surface of the beveled portion.

It is contemplated for the plurality of positioning recesses to be complementary to the plurality of positioning protrusions.

It is also contemplated for the plurality of positioning recesses to be aligned with the at least one membrane slit.

Still further, it is contemplated for the plurality of positioning protrusions to be alternately disposed with the plurality of positioning recesses around a circumference of the annular wall.

The at least one membrane slit may include any number of slits that divide the membrane into any number of flaps. For instance, in certain embodiments of the disclosure, the at least one membrane slit is a single membrane slit that divides the membrane into two symmetrical flaps, while in an alternative embodiment of the disclosure, the at least one membrane slit includes three membrane slits that divide the membrane into three congruent flaps.

Each ligament slit can form an angle between 80 degrees and 90 degrees with the membrane.

Also disclosed herein is a hemostasis valve, including a first valve gasket and a second valve gasket. The first valve gasket includes: an annular wall; a plurality of ligaments attached to and extending radially inward from the annular wall, wherein each ligament of the plurality of ligaments includes a ligament slit that divides the ligament into two ligament segments; and a membrane surrounded by the annular wall and attached to the plurality of ligaments and to the annular wall, wherein the membrane includes at least one membrane slit that divides the membrane into a plurality of flaps, wherein the plurality of ligaments are positioned with the plurality of ligament slits aligned with the at least one membrane slit, such that each flap is bounded along a circumferential edge by the annular wall, along a first radial edge by a first ligament segment, and along a second radial edge by a second ligament segment. The second valve gasket likewise includes: an annular wall; a plurality of ligaments attached to and extending radially inward from the annular wall, wherein each ligament of the plurality of ligaments includes a ligament slit that divides the ligament into two ligament segments; and a membrane surrounded by the annular wall and attached to the plurality of ligaments and to the annular wall, wherein the membrane includes at least one membrane slit that divides the membrane into a plurality of flaps, wherein the plurality of ligaments are positioned with the plurality of ligament slits aligned with the at least one membrane slit, such that each flap is bounded along a circumferential edge by the annular wall, along a first radial edge by a first ligament segment, and along a second radial edge by a second ligament segment. A rear surface of the first valve gasket is placed against a rear surface of the second valve gasket with the membrane of the first valve gasket pressed against the membrane of the second valve gasket.

The first valve gasket of the hemostasis valve may further include a central protrusion positioned on the membrane of the first valve gasket, wherein the plurality of ligaments of the first valve gasket connect to the central protrusion of the first valve gasket. The second valve gasket of the hemostasis valve may similarly include a central protrusion positioned on the membrane of the second valve gasket, wherein the plurality of ligaments of the second valve gasket connect to the central protrusion of the second valve gasket. At least one of the central protrusion of the first valve gasket and the central protrusion of the second valve gasket can include a guiding recess.

According to aspects of the disclosure, the annular wall of the first valve gasket includes: a cylindrical portion; a beveled portion; a plurality of positioning protrusions extending from an exit surface of the cylindrical portion; and a plurality of positioning recesses extending radially into the beveled portion. The annular wall of the second valve gasket can likewise include: a cylindrical portion; a beveled portion; a plurality of positioning protrusions extending from an exit surface of the cylindrical portion; and a plurality of positioning recesses extending radially into the beveled portion. Within the hemostasis valve, the first valve gasket is placed against the second valve gasket such that the positioning protrusions of the annular wall of the first valve gasket fit within the positioning recesses of the annular wall of the second valve gasket and the positioning protrusions of the annular wall of the second valve gasket fit within the positioning recesses of the annular wall of the first valve gasket. To facilitate such assembly, the positioning protrusions of the annular wall of the first valve gasket can be complementary to the positioning recesses of the annular wall of the second valve gasket, and the positioning protrusions of the annular wall of the second valve gasket can be complementary to the positioning recesses of the annular wall of the first valve gasket.

To improve sealing characteristics of the hemostasis valve, it is further contemplated that the positioning recesses of the first valve gasket can be aligned with the at least one membrane slit of the first valve gasket, and the positioning recesses of the second valve gasket can be aligned with the at least one membrane slit of the second valve gasket, such that, when the rear surface of the first valve gasket is placed against the rear surface of the second valve gasket, the at least one membrane slit of the first valve gasket is rotationally offset from the at least one membrane slit of the second valve gasket.

The first and second valve gaskets may be disposed within a rigid valve housing.

The first valve gasket can be structurally identical to the second valve gasket.

The instant disclosure also provides a valve gasket, including an annular wall and a sealing assembly disposed within the annular wall, wherein the sealing assembly includes: a central protrusion; a plurality of ligaments connected to the central protrusion, wherein each ligament of the plurality of ligaments extends radially away from the central protrusion towards the annular wall and is connected to the annular wall; a membrane connected to the central protrusion, to the plurality of ligaments, and to the annular wall; and at least one slit through the membrane, the central protrusion, and the plurality of ligaments, wherein the at least one slit separates the sealing assembly into a plurality of flaps, wherein each flap of the plurality of flaps is bounded on an outer circumferential edge by the annular wall, on an inner circumferential edge by the central protrusion, on a first radial edge by a first ligament of the plurality of ligaments, and on a second radial edge by a second ligament of the plurality of ligaments.

The central protrusion can include a guiding recess.

The valve gasket can also include a plurality of spaced-apart positioning protrusions extending axially from a first (e.g., cylindrical) portion of the annular wall and a plurality of positioning recesses set into a circumferential surface of a second (e.g., beveled) portion of the annular wall, wherein the plurality of positioning protrusions are alternately disposed with the plurality of positioning recesses around a circumference of the annular wall.

The foregoing and other aspects, features, details, utilities, and advantages of the present invention will be apparent from reading the following description and claims, and from reviewing the accompanying drawings.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The instant disclosure provides various valve gaskets as well as hemostasis valve systems and cardiovascular introducers with cannula units incorporating the same. For purposes of illustration, aspects of the disclosure will be described with reference to the introduction of an interventional medical device into a patient's vasculature. Those of ordinary skill in the art, however, will appreciate that the instant teachings may be applied to good advantage in other contexts.

Figure 1:
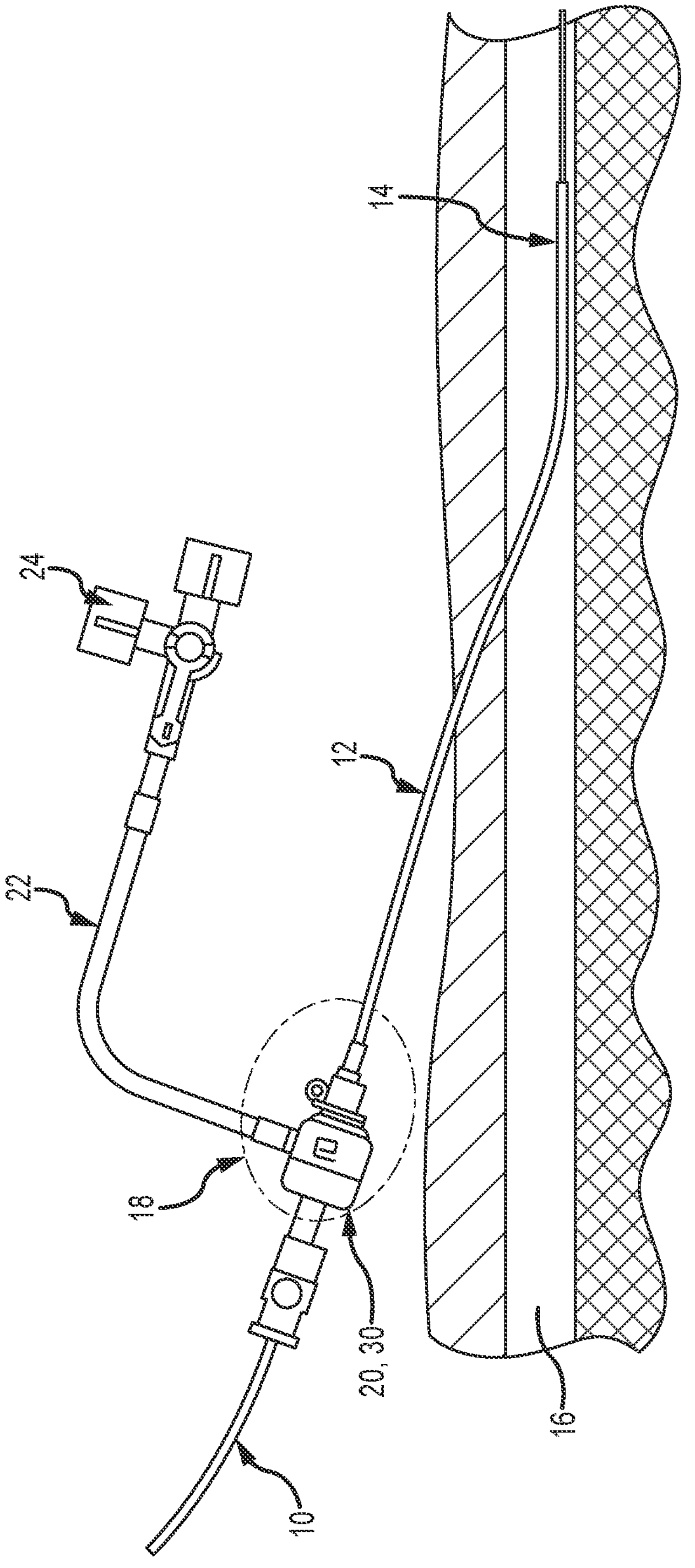
FIG. 1 is a side, partially cut-away view illustration of the Seldinger technique for vascular access.

FIG. 1 depicts the introduction of various medical devices, including guidewire 10, cardiovascular introducer 18, and dilator 14, into a blood vessel 16 using the Seldinger technique. Insofar as the ordinarily skilled artisan will be familiar with the Seldinger technique, it need not be described in further detail herein.

Figure 2:
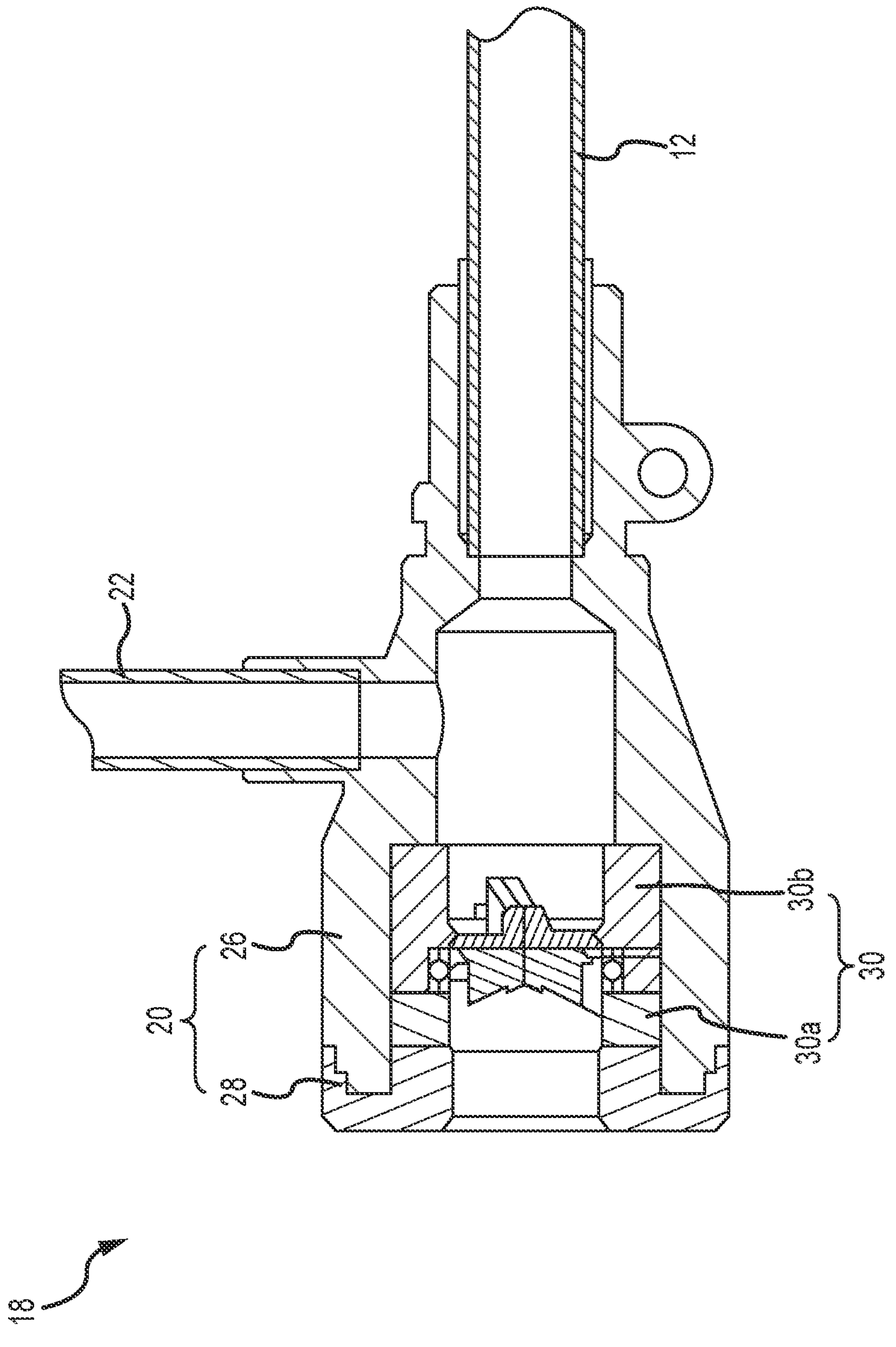
FIG. 2 is a cross-sectional view of a representative cardiovascular introducer comprising a cannula unit within which an integral hemostasis valve system is disposed.

As FIG. 1 illustrates, cardiovascular introducer 18 includes an introducer sheath 12, a cannula unit 20, a hemostasis valve system 30, and a side-port fluid tubing 22 with an associated stopcock assembly 24. As shown in FIG. 2, cannula unit 20 is comprised of a cap 28 and a housing 26 circumferentially sealed together, within which integral hemostasis valve system 30 (e.g., a fully assembled unit of two valve gaskets 30*a* and 30*b* as described herein), is disposed at its proximal end. Side-port fluid tubing 22 and associated stopcock assembly 24 are also coupled to cannula unit 20 or housing 26 to enable the introduction of medical fluids (e.g., saline) through introducer 18 or introducer sheath 12 for an intended clinical procedure.

FIG. 2 is a cross-sectional view of cardiovascular introducer 18 incorporating an integral hemostasis valve system 30 within a circumferentially sealed cannula unit 20. Various details of cannula unit 20, including housing 26 and cap 28, will be familiar to those of ordinary skill in the art; thus, cannula unit 20 will only be described herein to the extent necessary to understand the instant disclosure.

The exterior of cannula unit 20 is defined by a housing 26 and a cap 28. Contained within circumferentially sealed housing 26 by cap 28 are a first (or proximal) valve gasket 30*a* and a second (or distal) valve gasket 30*b*, the structures and arrangements of which are described in greater detail below. As fully assembled and constrained within housing 26, first and second valve gaskets 30*a*, 30*b* collectively constitute a hemostasis valve system 30.

In embodiments of the disclosure, first and second valve gaskets 30*a*, 30*b* are structurally identical to each other and are oriented back-to-back within housing 26. Accordingly, it should be understood that the descriptions of various valve gasket embodiments herein are equally applicable to either, or both, of valve gaskets 30*a*, 30*b*.

Each of valve gaskets 30*a*, 30*b* has two axial faces, one facing proximally and one facing distally. For convenience and ease of reference, the first (e.g., proximally-facing) axial face of a valve gasket will be referred to herein as the "entry face," while the second (e.g., distally-facing) axial face of a valve gasket will be referred to herein as the "exit face." This same naming convention will be utilized to refer to the various surfaces of the valve gasket embodiments described herein (that is, proximally-facing surfaces will be referred to as "entry faces," while distally-facing surfaces will be referred to as "exit faces"). It will become apparent to those of ordinary skill in the art from reviewing this disclosure, however, that this naming convention follows from the orientation of first valve gasket 30*a*, and would be reversed when referring to second valve gasket 30*b*, the orientation of which is reversed relative to first valve gasket 30*a* as mentioned above and described in greater detail below.

Figure 3B:
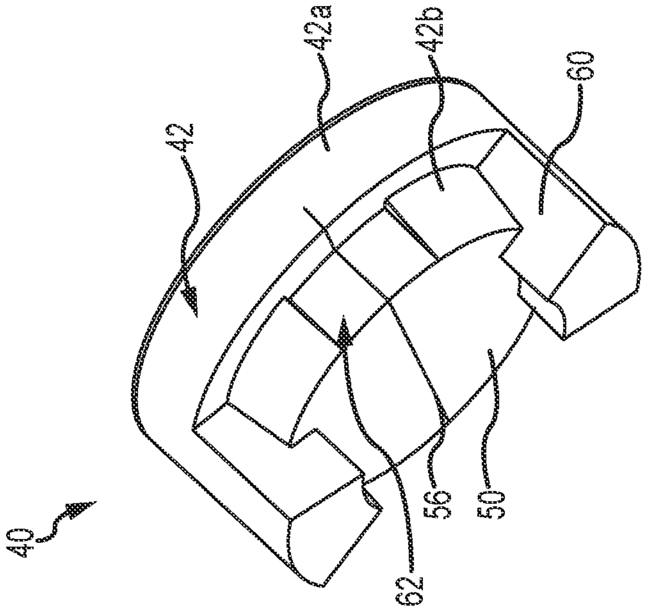
FIG. 3B is an exit face perspective view of a biomimetic bicuspid valve gasket as disclosed herein.
Figure 3A:
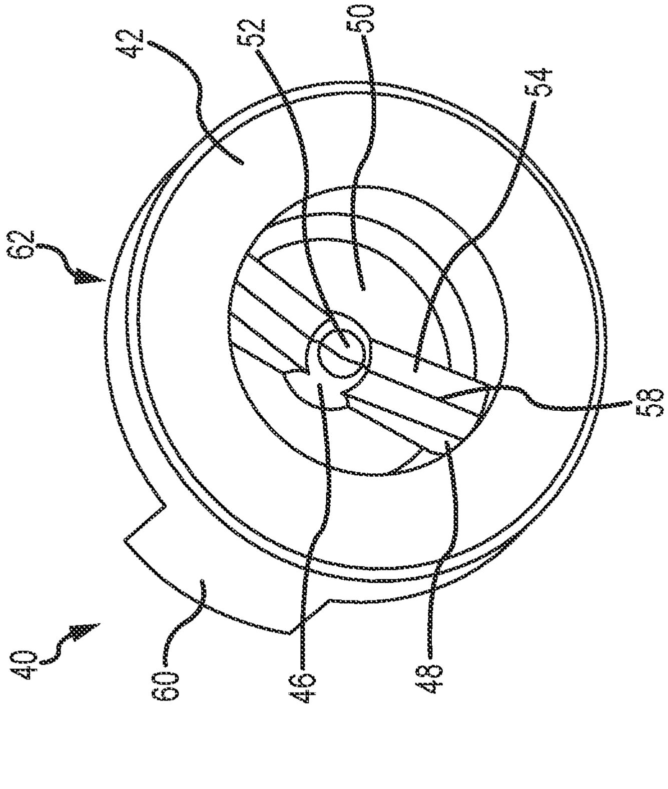
FIG. 3A is an entry face perspective view of a biomimetic bicuspid valve gasket as disclosed herein.
Figure 3D:
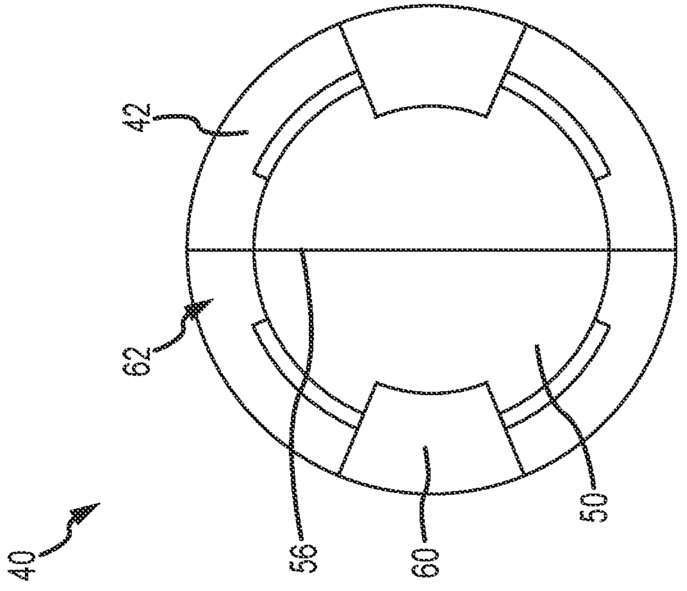
FIG. 3D is an exit face planar view of the biomimetic bicuspid valve gasket shown in FIGS. 3A and 3B.
Figure 3C:
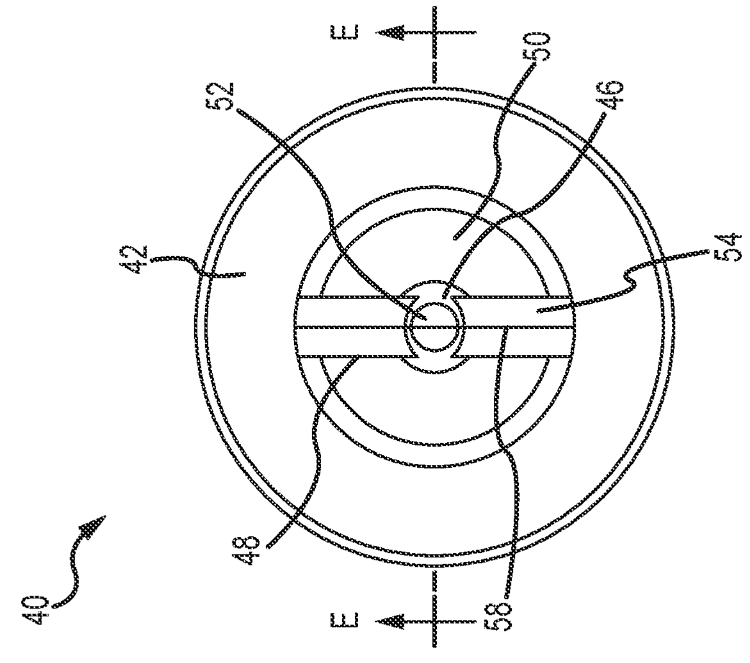
FIG. 3C is an entry face planar view of the biomimetic bicuspid valve gasket shown in FIGS. 3A and 3B.
Figure 3E:
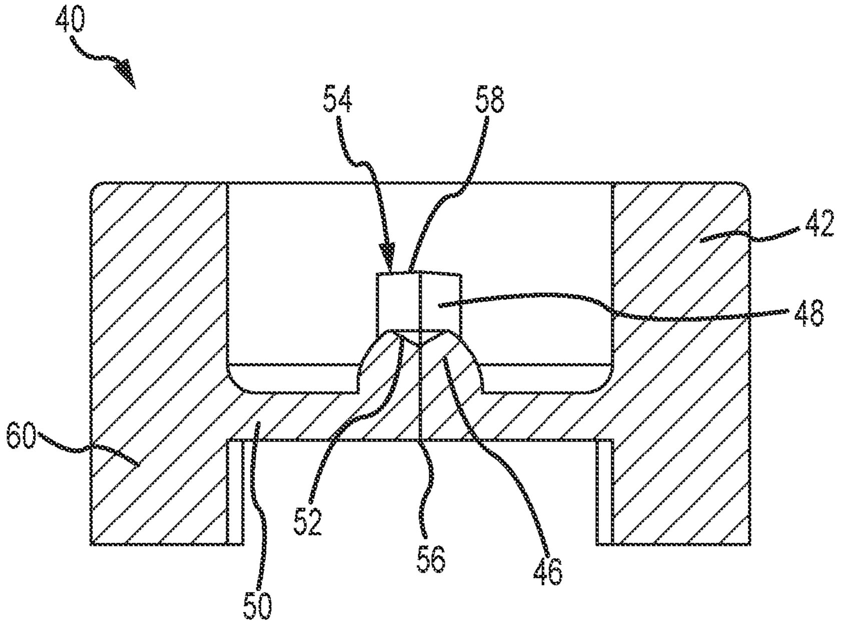
FIG. 3E is a sectional view taken along line E-E in FIG. 3C.

FIGS. 3A-3E are various views of a valve gasket 40 according to a first embodiment disclosed herein. For reasons that will be clear upon reviewing the following disclosure, the embodiment of FIGS. 3A-3E can be referred to as a "biomimetic bicuspid valve gasket" (or simply a "bicuspid valve gasket"). FIGS. 3A and 3B are perspective views of bicuspid valve gasket 40, with FIG. 3A emphasizing the entry face of bicuspid valve gasket 40 and FIG. 3B emphasizing the exit face of bicuspid valve gasket 40. FIG. 3C is a planar view looking towards the entry face of bicuspid valve gasket 40. FIG. 3D is a planar view looking towards the exit face of bicuspid valve gasket 40. FIG. 3E is a cross-sectional view taken along line E-E in FIG. 3C.

Bicuspid valve gasket 40 includes an annular wall 42, a central protrusion 46, a plurality of ligaments 48, and a disc-shaped valve membrane 50. Ligaments 48 extend radially from central protrusion 46 to annular wall 42, and are attached to both. Likewise, valve membrane 50 is attached to annular wall 42, central protrusion 46, and ligaments 48. In some embodiments of the disclosure, bicuspid valve gasket 40 may be formed as a unitary assembly, such as by reactive injection molding, or reactive compression molding, with use of a liquid or gum-like silicone rubber material. And, although all elements may be integrally formed, the term "sealing assembly" will be used herein as a shorthand to refer collectively to valve membrane 50, central protrusion 46, and ligaments 48.

Central protrusion 46 is centrally located within annular wall 42 and protrudes from the entry face of valve membrane 50. That is, central protrusion 46 is positioned on valve membrane 50 and has an axial centerline that is substantially coincident with the axial centerline of the annulus defined by annular wall 42. Central protrusion 46 may be cylindrical, hemispherical, or any other shape suitable to the interconnection of ligaments 48 as described below (e.g., a square-shaped central protrusion could be used in a four-ligament configuration).

To aid in the insertion of an interventional medical device (e.g., guidewire 10 and/or dilator 14) through a hemostasis valve system 20, central protrusion 46 can include a guiding recess 52, which can be formed in the nature of a depression into the entry face of central protrusion 46. Guiding recess 52 may be conical, cylindrical, or any other suitable shape to help guide an interventional medical device towards the center of bicuspid valve gasket 40 during insertion. For instance, guiding recess 52 may have walls that slope conically inward, such that they are highest along the perimeter of guiding recess 52 and lowest near the center point of the annulus defined by annular wall 42.

As mentioned above, each ligament 48 is geometrically connected to both central protrusion 46 and annular wall 42 and extends generally along a radius of the annulus defined by annular wall 42 on the entry face of valve membrane 50 (e.g., in the nature of a wheel spoke). Each ligament 48 extends above the entry face of membrane 50 to an upper surface 54. Upper surface 54 may be parallel or inclined to the entry face of valve membrane 50; where upper surface 54 is inclined relative to the entry face of valve membrane 50, it is contemplated that the highest point of upper surface 54 will be where it meets annular wall 42 and that the lowest point of upper surface 54 will be where it meets central protrusion 46 (e.g., upper surface 54 of ligament 48 slopes downward towards central protrusion 46). This latter configuration is shown to good advantage in FIG. 4E.

As also mentioned above, valve membrane 50 is geometrically attached to annular wall 42, to central protrusion 46, and to each ligament 48. As explained in further detail below, these attachments support valve membrane 50, bias valve membrane 50 into a closed position (e.g., to prevent fluid leakage through bicuspid valve gasket 40), permit resilient, radial compression, or opening, under insertion forces imposed on the entry face (e.g., as an interventional medical device is inserted), and resist axial distension of valve membrane 50 under pressure (e.g., blood pressure) imposed on the exit face.

At least one slit 56 is formed through valve membrane 50. In the case of bicuspid valve gasket 40, slit 56 divides valve membrane 50, as well as central protrusion 46, into two substantially symmetrical flaps (also referred to as "segments," "valve flaps," or "leaflets").

Each ligament 48 likewise includes a slit therethrough. For example, as best illustrated in FIGS. 3A and 3C, each ligament 48 includes a ligament slit 58 that divides the respective ligament into two relatively symmetrical ligament segments.

In some embodiments of the disclosure, each ligament slit 58 can be perpendicular to valve membrane 50. In alternative embodiments, ligament slits 58 may be non-normal to valve membrane 50. Thus, it is contemplated that any given ligament slit 58 can form an angle of between about 70 degrees and about 90 degrees, and, more desirably, an angle of between about 80 degrees and about 90 degrees, with valve membrane 50. Where ligament slits 58 are non-normal to valve membrane 50, it is contemplated that they will be generally centered on the entry face of ligaments 48.

Ligaments 48 are arranged on valve membrane 50 such that their respective ligament slits 58 are planarly aligned with membrane slit(s) 56 (best illustrated in FIG. 3E). Indeed, ligament slits 58 can be formed at the same time as membrane slit(s) 56 by cutting through both valve membrane 50 and ligaments 48 at once.

As shown in FIGS. 3A-3E, bicuspid valve gasket 40 includes two ligaments 48 positioned about 180 degrees from each other (e.g., along slit 56). Thus, each of the two flaps of bicuspid valve gasket 40 is bounded along its outer circumferential edge by annular wall 42, along its inner circumferential edge by central protrusion 46, and on its radial edges by segments of ligaments 48.

As illustrated to good advantage in FIG. 3B, annular wall 42 includes a first, more proximal, generally cylindrical portion 42*a* and a second, more distal, beveled (or frustoconical) portion 42*b*. A plurality of positioning protrusions 60 extend in an axial direction from the exit face of generally cylindrical portion 42*a*. Correspondingly, a plurality of positioning recesses 62 are set radially into a circumferential surface of beveled portion 42*b*, in between respective positioning protrusions 60 and beveled surfaces 64. According to aspects of the disclosure, positioning protrusions 60 alternate with positioning recesses 62 around the circumference of annular wall 42.

In some embodiments of the disclosure, the plurality of positioning recesses 62 are geometrically complementary to the plurality of positioning protrusions 60. For example, each positioning recess 62 can include a convex surface that is configured to mate with a corresponding concave surface on a respective positioning protrusion 60.

According to aspects of the disclosure, the plurality of positioning recesses 62 are substantially aligned with membrane slit(s) 56. Thus, for example, bicuspid valve gasket 40 includes two positioning protrusions 60 and two positioning recesses 62, alternately disposed around annular wall 42 at about 90-degree intervals. As described further below, this configuration helps ensure that a hemostasis valve system 20 including two bicuspid valve gaskets 40 arranged back-to-back will achieve a good seal. Of course, the same result could be achieved equally well with the plurality of positioning protrusions 60 aligned with the membrane slit(s) 56.

Figure 4B:
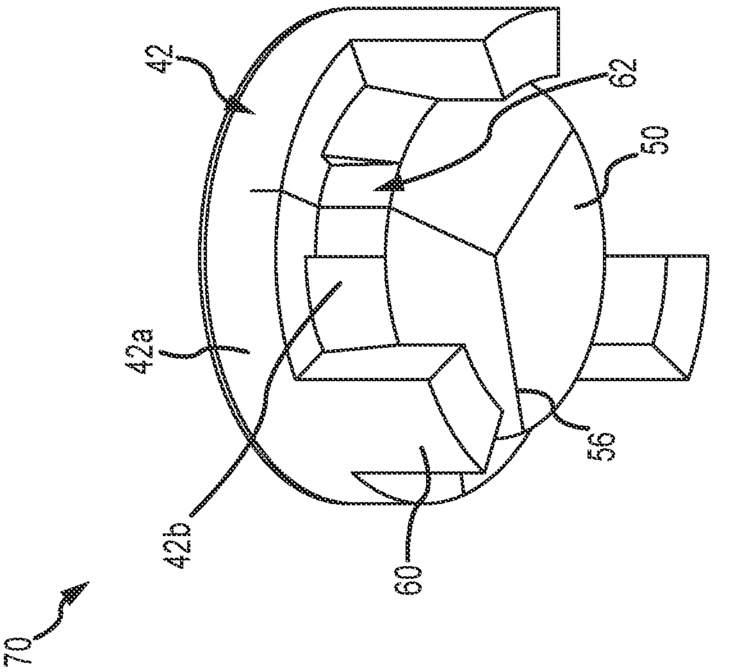
FIG. 4B is an exit face perspective view of a biomimetic tricuspid valve gasket as disclosed herein.
Figure 4A:
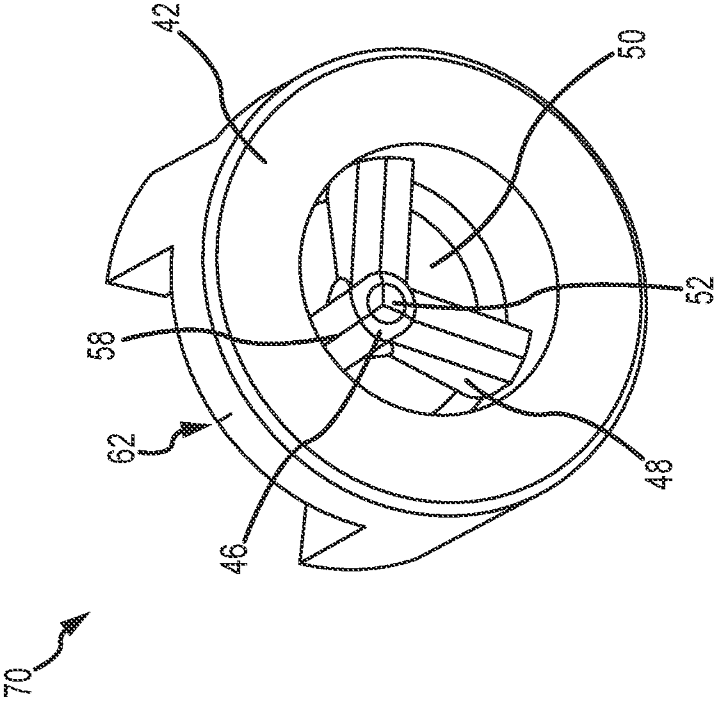
FIG. 4A is an entry face perspective view of a biomimetic tricuspid valve gasket as disclosed herein.
Figure 4D:
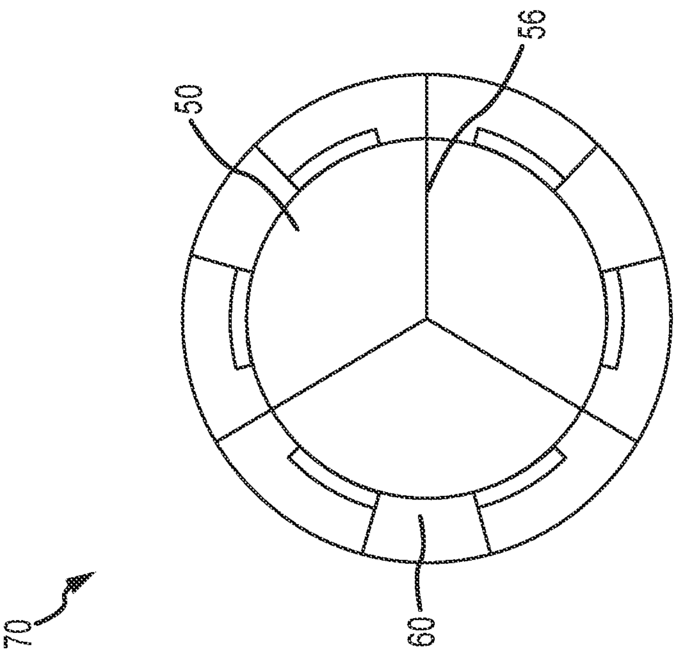
FIG. 4D is an exit face planar view of the tricuspid valve gasket shown in FIGS. 4A and 4B.
Figure 4C:
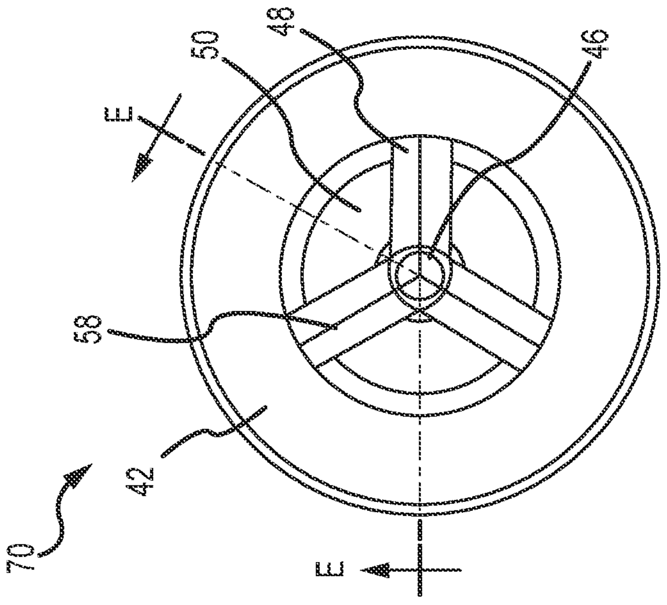
FIG. 4C is an entry face planar view of the biomimetic tricuspid valve gasket shown in FIGS. 4A and 4B.
Figure 4E:
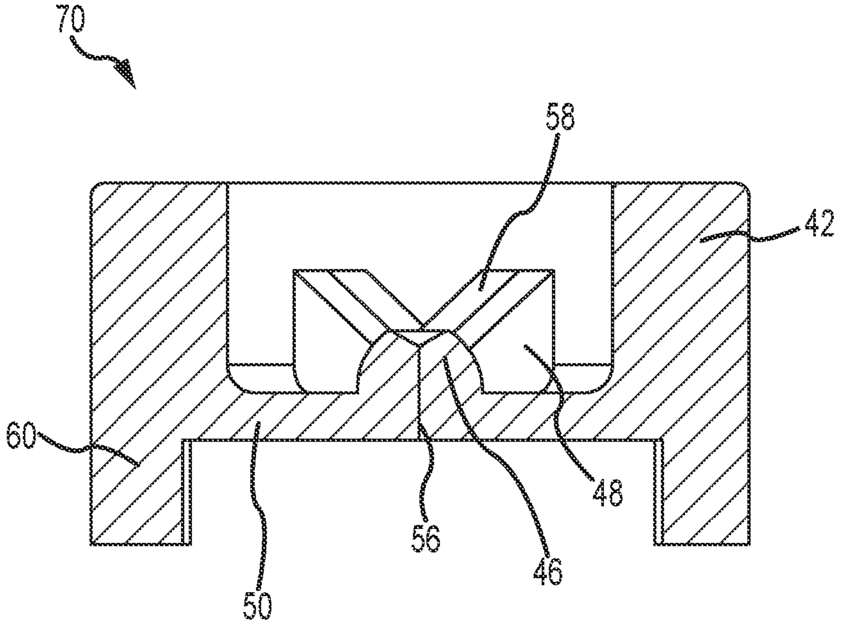
FIG. 4E is a sectional view taken along line E-E in FIG. 4C.

FIGS. 4A-4E are various views of a valve gasket 70 according to a second embodiment disclosed herein. For reasons that will be clear upon reviewing the following disclosure, the embodiment of FIGS. 4A-4E can be referred to as a "biomimetic tricuspid valve gasket" (or simply a "tricuspid valve gasket"). FIGS. 4A and 4B are perspective views of tricuspid valve gasket 70, with FIG. 4A emphasizing the entry face of tricuspid valve gasket 70 and FIG. 4B emphasizing the exit face of tricuspid valve gasket 70. FIG. 4C is a planar view looking towards the entry face of tricuspid valve gasket 70. FIG. 4D is a planar view looking towards the exit face of tricuspid valve gasket 70. FIG. 4E is a cross-sectional view taken along line E-E in FIG. 4C.

Tricuspid valve gasket 70 shares many structural features in common with bicuspid valve gasket 40. For example, tricuspid valve gasket 70 includes an annular wall 42 (having both a generally cylindrical portion 42*a* and a beveled or frustoconical portion 42*b*), a central protrusion 46 with guiding recess 52, a plurality of ligaments 48, and a valve membrane 50. Likewise, central protrusion 46 and valve membrane 50 include slits 56 therethrough, with ligaments 48 similarly including ligament slits 58.

Tricuspid valve gasket 70 also includes a plurality of positioning protrusions 60, beveled surfaces 64, and positioning recesses 62 therebetween. In particular, tricuspid valve gasket 70 includes three positioning protrusions 60 and three positioning recesses 62, alternately disposed around annular wall 52 at about 60-degree intervals.

Tricuspid valve gasket 70 differs, however, in the number of ligaments 48, membrane slits 56, and ligament slits 58. Specifically, tricuspid valve gasket 70 includes three ligaments 48 with corresponding ligament slits 58 and three slits 56 through membrane 50 and central protrusion 46. Ligaments 48 and slits 56 are disposed at about 120 degree intervals, thus dividing sealing assembly 44 of tricuspid valve gasket 70 into three substantially congruent flaps. As with bicuspid valve gasket 40, each flap is bounded along its outer circumferential edge by annular wall 42, along its inner circumferential edge by central protrusion 46, and along its radial edges by segments of ligaments 48.

Figure 5B:
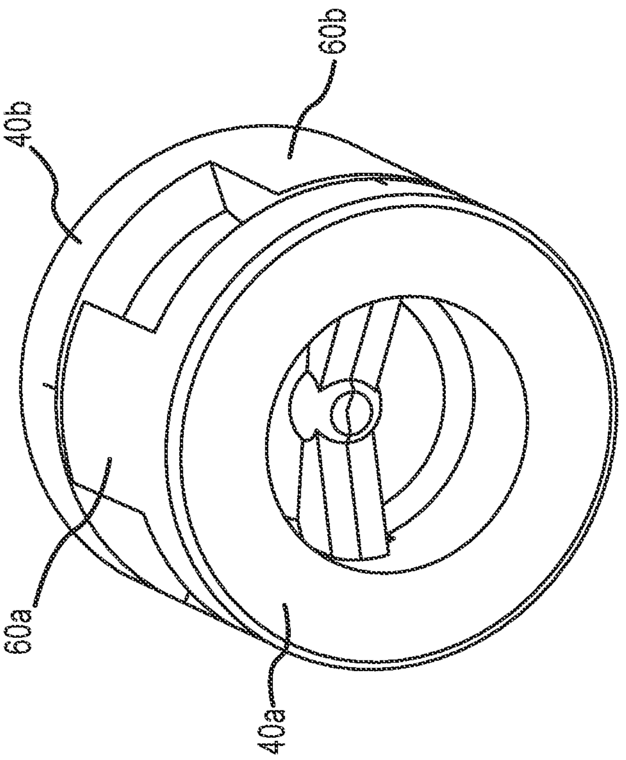
FIG. 5B illustrates a pair of biomimetic bicuspid valve gaskets fully assembled into an integral hemostasis valve system for use, for example, in a cardiovascular introducer such as shown in FIG. 2.
Figure 5A:
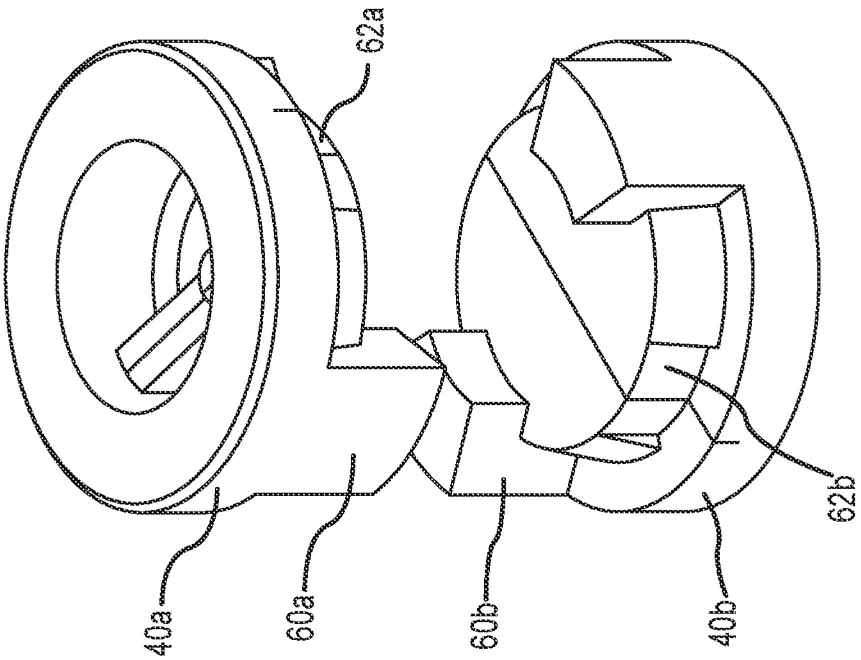
FIG. 5A illustrates a pair of biomimetic bicuspid valve gaskets to be assembled into a hemostasis valve system.
Figure 6B:
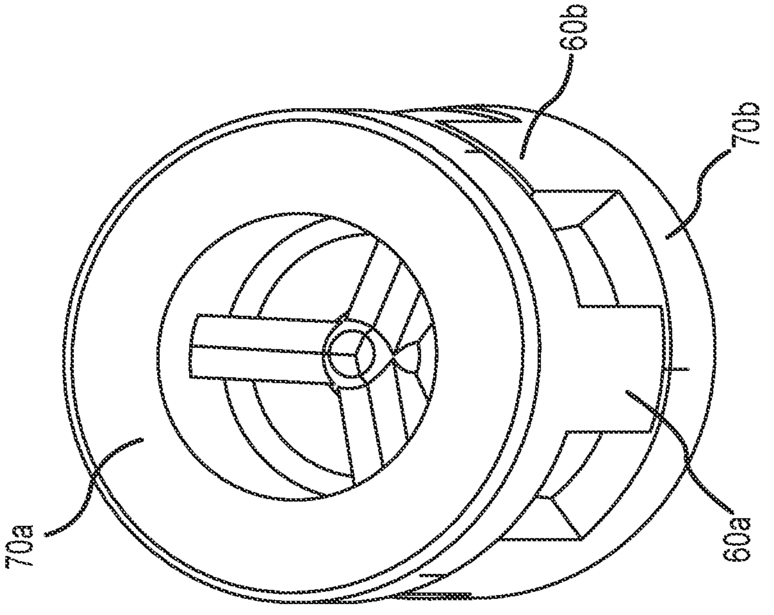
FIG. 6B illustrates a pair of biomimetic tricuspid valve gaskets fully assembled into an integral hemostasis valve system for use, for example, in a cardiovascular introducer such as shown in FIG. 2.
Figure 6A:
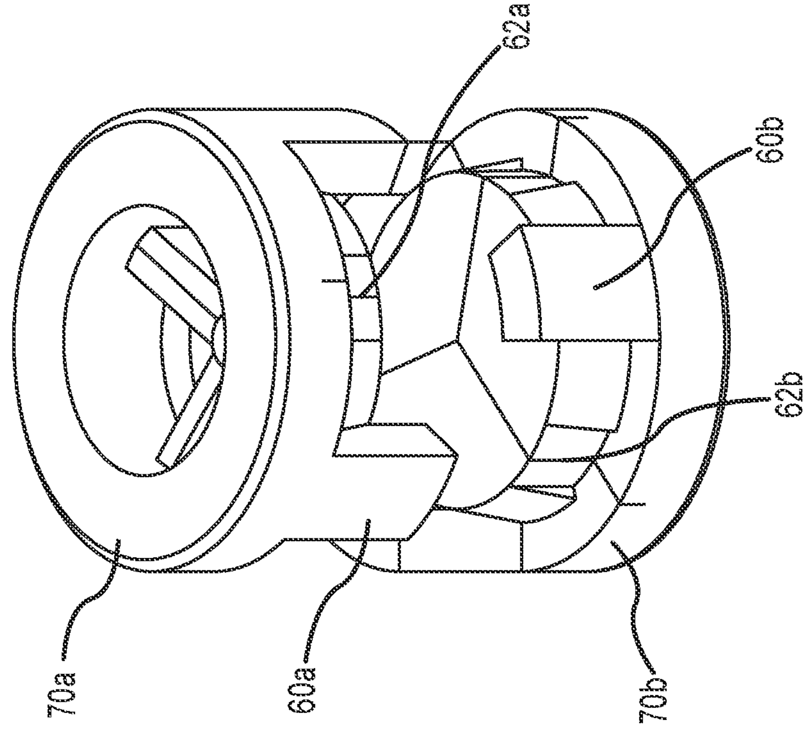
FIG. 6A illustrates a pair of biomimetic tricuspid hemostasis valve gaskets to be assembled into a hemostasis valve system.

FIGS. 5A and 5B illustrate a hemostasis valve system 20 as an assembly of two bicuspid valve gaskets 40*a*, 40*b*. FIGS. 6A and 6B illustrate a hemostasis valve system 20 as another assembly of two tricuspid valve gaskets 70*a*, 70*b*.

In either case (and, indeed, in general in accordance with the instant teachings), the two valve gaskets 40*a*, 40*b* or 70*a*, 70*b* are positioned back-to-back (that is, exit face-to-exit face) such that the positioning protrusions 60*a* of the first gasket 40*a*, 70*a* mate into the positioning recesses 62*b* of the second gasket 40*b*, 70*b*, and vice versa, with tight interfacial contact between the respective valve membranes 50. Because valve membrane and ligament slits 56, 58 on each gasket 40*a*, 40*b* or 70*a*, 70*b* are aligned with the positioning recesses 62*a*, 62*b*, the slits 56, 58 on one valve gasket 40*a*, 70*a* will be rotationally offset from the slits 56, 58 on other valve gasket 40*b*, 70*b* when assembled together as shown and described.

For instance, slits 56, 58 on one valve gasket 40*a* will be rotationally offset by about 90 degrees from slits 56, 58 on the other valve gasket 40*b* when the two are assembled together with tight interfacial contact between the exit faces of their respective valve membranes. Similarly, slits 56, 58 on one valve gasket 70*a* will be rotationally offset by about 60 degrees from slits 56, 58 on the other valve gasket 70*b* when the two are assembled together with tight interfacial contact between the exit faces of their respective membranes.

Thus, any gap that forms between a flap of one valve gasket 40*a* or 70*a* and an interventional medical device inserted therethrough will be misaligned with any gap that forms between a flap of the other valve gasket 40*b* or 70*b* and the same interventional medical device. This ensures that a hemostasis valve system 20 achieves a good seal and prevents fluid passage through both valve gaskets 40*a*, 40*b* or 70*a*, 70*b*.

Likewise, the back-to-back configuration for assembling two valve gaskets and use of ligaments 48 on individual valve gaskets advantageously renders hemostasis valve system 20 according to the instant disclosure self-sealing. In particular, ligaments 48 will result in valve membranes 50 exhibiting a greater resistance to axial stretching than to radial or transverse compression when an interventional medical device is inserted or withdrawn through hemostasis valve system 20. This, in turn, will minimize axial deformation of the valve gaskets, and desirably reduce the potential for air embolism during the insertion and withdrawal of an interventional medical device.

That is, when an interventional medical device is inserted through the entry face of a valve gasket according to the instant disclosure, ligaments 48 will permit axial distension of the flaps. If, on the other hand, the interventional medical device is inserted through the exit face of the valve gasket, ligaments 48 will resist axial distension. Instead, both valve gaskets, as an integral hemostasis valve system 20, will be compressed radially, resulting in improved conformance to the outer profile of the interventional medical device and, in turn, a tighter seal against the interventional medical device.

Therefore, when two valve gaskets as disclosed herein are assembled in back-to-back arrangement, it does not matter from which direction an interventional medical device is inserted through hemostasis valve system 20. In either insertion direction, the ligaments 48 of one valve gasket will permit axial distension while the ligaments 48 of the other valve gasket will resist axial distension in favor of radial compression, thus minimizing the risk of air embolism.

Suitable materials for valve gaskets as disclosed herein include various compliant and highly elastic polymeric materials, as well as polymeric foams with high resiliency. These include, without limitation, silicone rubber, urethane rubber, natural rubber (isoprene), and other synthetic hydrocarbon rubber materials (e.g., ethylene-propylene-diene elastomer, styrene-butadiene rubber, neoprene rubber, nitrile or Buna-N rubber, butyl rubber, fluoroelastomers and the like). Certain thermoplastic elastomers (e.g., styrenic, olefinic, polyester-based, and polyamide-based block copolymers and the like) and/or thermoplastic vulcanizates (e.g., thermoplastic polypropylene with vulcanized silicone rubber, thermoplastic polyurethane with vulcanized silicone rubber, and the like) may also be suitable.

Although several embodiments have been described above with a certain degree of particularity, those skilled in the art could make numerous alterations to the disclosed embodiments without departing from the spirit or scope of this invention.

For example, although biomimetic bicuspid and tricuspid valve gasket embodiments have been described in detail above, it should be understood that the teachings herein can be applied to a valve gasket with any number of flaps (or segments), including configurations that may not be biomimetic.

Figure 7A:
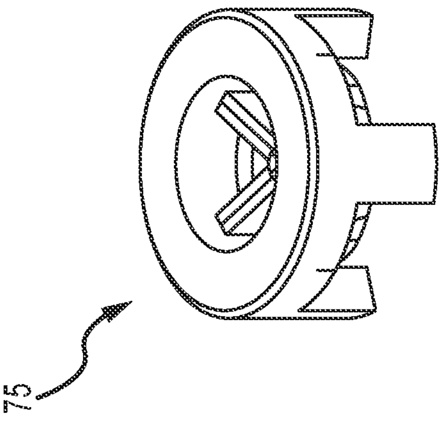
FIG. 7A is an entry face perspective view of a valve gasket including four flaps as disclosed herein.
Figure 7B:
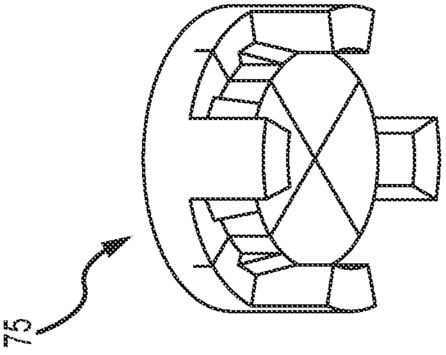
FIG. 7B is an exit face perspective view of a valve gasket including four flaps as disclosed herein.
Figure 7C:
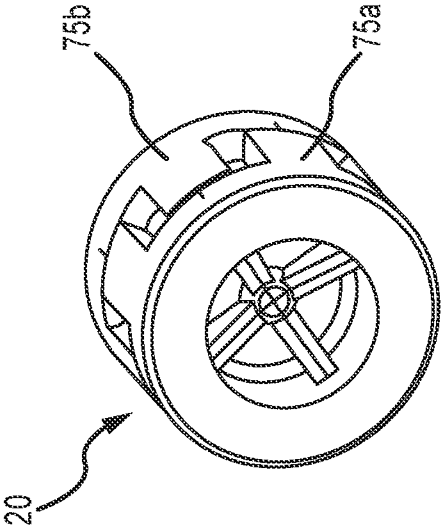
FIG. 7C illustrates a pair of valve gaskets including four flaps fully assembled into an integral hemostasis valve system for use, for example, in a cardiovascular introducer such as shown in FIG. 2.
Figure 8A:
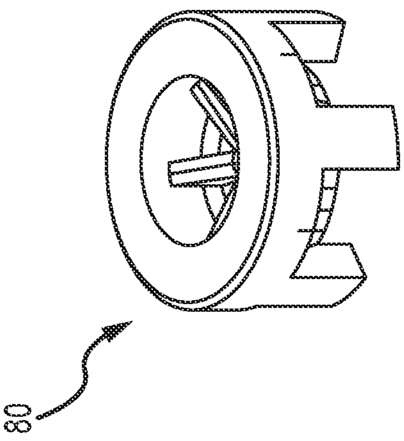
FIG. 8A is an entry face perspective view of a valve gasket including five flaps as disclosed herein.
Figure 8B:
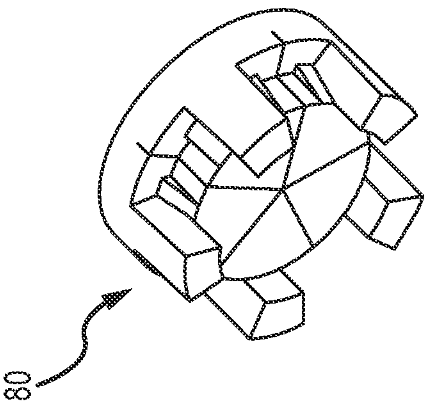
FIG. 8B is an exit face perspective view of a valve gasket including five flaps as disclosed herein.
Figure 8C:
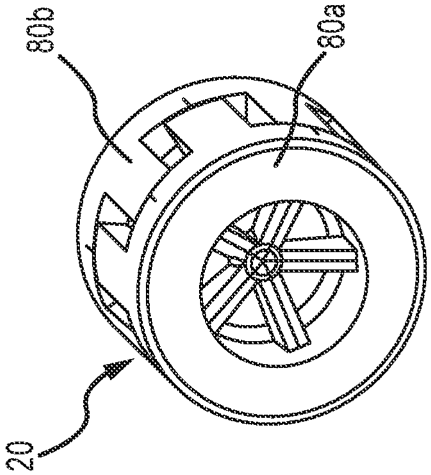
FIG. 8C illustrates a pair of valve gaskets including five flaps fully assembled into an integral hemostasis valve system for use, for example, in a cardiovascular introducer such as shown in FIG. 2.

In this regard, FIGS. 7A-7C depict a valve gasket 75 that includes four substantially congruent flaps, and a hemostasis valve assembly 20 utilizing two such gaskets 75*a*, 75*b*, while FIGS. 8A-8C depict a valve gasket 80 that includes five substantially congruent flaps, and a hemostasis valve assembly 20 utilizing two such gaskets 80*a*, 80*b*. It should be understood that valve gaskets 75 and 80 share many structural features in common with bicuspid valve gasket 40 and tricuspid valve gasket 70, and differ primarily in the number of flaps and the number and placement of ligaments, slits, positioning protrusions, and positioning recesses.

As another example, the flaps (or segments) need not be substantially equal in size, as results from regular spacing of the ligaments and slits around the central protrusion. Instead, the ligaments and slits can be positioned at irregular intervals around the central protrusion, yielding some flaps (or segments) that are larger than others.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A valve gasket, comprising:

an annular wall;

a plurality of ligaments attached to and extending radially inward from the annular wall, wherein each ligament of the plurality of ligaments has an upper surface that slopes downward and radially inward from the annular wall, and wherein each ligament of the plurality of ligaments includes a ligament slit that divides the ligament into two ligament segments; and a membrane surrounded by the annular wall and attached to the plurality of ligaments and to the annular wall, wherein the membrane includes at least one membrane slit that divides the membrane into a plurality of flaps, wherein the plurality of ligaments are positioned with the plurality of ligament slits aligned with the at least one membrane slit, such that each flap has a perimeter defined by the annular wall, a first ligament segment, and a second ligament segment.

2. The valve gasket according to claim 1, further comprising a central protrusion positioned on the membrane, wherein the plurality of ligaments connect to the central protrusion.

3. The valve gasket according to claim 2, wherein the central protrusion comprises a guiding recess.

4. The valve gasket according to claim 1, wherein the annular wall comprises:

a cylindrical portion;

a beveled portion;

a plurality of positioning protrusions extending axially from an exit surface of the cylindrical portion; and a plurality of positioning recesses set radially into a circumferential surface of the beveled portion.

5. The valve gasket according to claim 4, wherein the plurality of positioning recesses are complementary to the plurality of positioning protrusions.

6. The valve gasket according to claim 4, wherein the plurality of positioning recesses are aligned with the at least one membrane slit.

7. The valve gasket according to claim 4, wherein the plurality of positioning protrusions are alternately disposed with the plurality of positioning recesses around a circumference of the annular wall.

8. The valve gasket according to claim 1, wherein the at least one membrane slit comprises a single membrane slit that divides the membrane into two symmetrical flaps.

9. The valve gasket according to claim 1, wherein the at least one membrane slit comprises three membrane slits that divide the membrane into three congruent flaps.

10. The valve gasket according to claim 1, wherein the ligament slit of each ligament forms an angle between 80 degrees and 90 degrees with the membrane.

11. A hemostasis valve, comprising:

a first valve gasket, comprising:

an annular wall;

a plurality of ligaments attached to and extending radially inward from the annular wall, wherein each ligament of the plurality of ligaments has an upper surface that slopes downward and radially inward from the annular wall, and wherein each ligament of the plurality of ligaments includes a ligament slit that divides the ligament into two ligament segments; and a membrane surrounded by the annular wall and attached to the plurality of ligaments and to the annular wall, wherein the membrane includes at least one membrane slit that divides the membrane into a plurality of flaps, wherein the plurality of ligaments are positioned with the plurality of ligament slits aligned with the at least one membrane slit, such that each flap has a perimeter defined by the annular wall, a first ligament segment, and a second ligament segment; and a second valve gasket, comprising:

an annular wall;

a plurality of ligaments attached to and extending radially inward from the annular wall, wherein each ligament of the plurality of ligaments has an upper surface that slopes downward and radially inward from the annular wall, and wherein each ligament of the plurality of ligaments includes a ligament slit that divides the ligament into two ligament segments; and a membrane surrounded by the annular wall and attached to the plurality of ligaments and to the annular wall, wherein the membrane includes at least one membrane slit that divides the membrane into a plurality of flaps, wherein the plurality of ligaments are positioned with the plurality of ligament slits aligned with the at least one membrane slit, such that each flap has a perimeter defined by the annular wall, a first ligament segment, and a second ligament segment, wherein a rear surface of the first valve gasket is placed against a rear surface of the second valve gasket with the membrane of the first valve gasket pressed against the membrane of the second valve gasket.

12. The hemostasis valve according to claim 11, wherein:

the first valve gasket further comprises a central protrusion positioned on the membrane of the first valve gasket, wherein the plurality of ligaments of the first valve gasket connect to the central protrusion of the first valve gasket; and the second valve gasket further comprises a central protrusion positioned on the membrane of the second valve gasket, wherein the plurality of ligaments of the second valve gasket connect to the central protrusion of the second valve gasket.

13. The hemostasis valve according to claim 12, wherein at least one of the central protrusion of the first valve gasket and the central protrusion of the second valve gasket further comprises a guiding recess.

14. The hemostasis valve according to claim 11, wherein:

the annular wall of the first valve gasket comprises:

a cylindrical portion;

a beveled portion;

a plurality of positioning protrusions extending axially from an exit surface of the cylindrical portion; and a plurality of positioning recesses set radially into a circumferential surface of the beveled portion;

the annular wall of the second valve gasket comprises:

a cylindrical portion;

a beveled portion;

a plurality of positioning protrusions extending axially from an exit surface of the cylindrical portion; and a plurality of positioning recesses set radially into a circumferential surface of the beveled portion; and the first valve gasket is placed against the second valve gasket such that the positioning protrusions of the annular wall of the first valve gasket fit within the positioning recesses of the annular wall of the second valve gasket and the positioning protrusions of the annular wall of the second valve gasket fit within the positioning recesses of the annular wall of the first valve gasket.

15. The hemostasis valve according to claim 14, wherein:

the positioning protrusions of the annular wall of the first valve gasket are complementary to the positioning recesses of the annular wall of the second valve gasket, and the positioning protrusions of the annular wall of the second valve gasket are complementary to the positioning recesses of the annular wall of the first valve gasket.

16. The hemostasis valve according to claim 14, wherein:

the positioning recesses of the first valve gasket are aligned with the at least one membrane slit of the first valve gasket, and the positioning recesses of the second valve gasket are aligned with the at least one membrane slit of the second valve gasket, such that, when the rear surface of the first valve gasket is placed against the rear surface of the second valve gasket, the at least one membrane slit of the first valve gasket is rotationally offset from the at least one membrane slit of the second valve gasket.

17. The hemostasis valve according to claim 11, further comprising a rigid valve housing, and wherein the first valve gasket and second valve gasket are disposed within the rigid valve housing.

18. The hemostasis valve according to claim 11, wherein the first valve gasket is structurally identical to the second valve gasket.

19. A valve gasket, comprising:

an annular wall; and a sealing assembly disposed within the annular wall, the sealing assembly comprising:

a central protrusion;

a plurality of ligaments connected to the central protrusion, wherein each ligament of the plurality of ligaments extends radially away from the central protrusion towards the annular wall and is connected to the annular wall, and wherein each ligament of the plurality of ligaments has an upper surface that slopes upward and radially away from the central protrusion towards the annular wall, and;

a membrane connected to the central protrusion, to the plurality of ligaments, and to the annular wall; and at least one slit through the membrane, the central protrusion, and the plurality of ligaments, wherein the at least one slit separates the sealing assembly into a plurality of valve flaps, wherein each valve flap of the plurality of valve flaps has a perimeter defined by the annular wall, the central protrusion, a first ligament of the plurality of ligaments, and a second ligament of the plurality of ligaments.

20. The valve gasket according to claim 19, wherein the central protrusion further comprises a guiding recess.

21. The valve gasket according to claim 19, further comprising a plurality of spaced-apart positioning protrusions extending axially from a first portion of the annular wall and a plurality of positioning recesses set into a circumferential surface of a second portion of the annular wall, wherein the plurality of positioning protrusions are alternately disposed with the plurality of positioning recesses around a circumference of the annular wall.

* * * * *